United States Patent [19]

Malin

[11] Patent Number: 5,858,794
[45] Date of Patent: Jan. 12, 1999

[54] CYANIDE-CONTAINING HEMOGLOBIN REAGENT COMPOSITION AND METHOD PROVIDING ACCEPTABLE PRECISION, ACCURACY AND FREEDOM FROM WHITE CELL INTERFERENCE ON AUTOMATED HEMATOLOGY ANALYZERS

[75] Inventor: Michael J. Malin, Park Ridge, N.J.

[73] Assignee: Bayer Corporation, Tarrytown, N.Y.

[21] Appl. No.: 854,914

[22] Filed: May 13, 1997

[51] Int. Cl.$^6$ .................................................. G01N 33/72
[52] U.S. Cl. .................................. 436/66; 436/8; 436/17; 436/18; 436/63; 436/175; 435/2; 252/408.1
[58] Field of Search .................................. 436/8, 10, 15, 436/16, 17, 18, 63, 66, 67, 174, 175; 435/2; 252/408.1

[56] References Cited

U.S. PATENT DOCUMENTS

| | | | |
|---|---|---|---|
| 3,874,852 | 4/1975 | Hammill | 436/63 |
| 4,853,338 | 8/1989 | Benezra et al. | 436/66 |
| 5,468,640 | 11/1995 | Benezra et al. | 436/66 |
| 5,612,223 | 3/1997 | Kim et al. | 436/17 |
| 5,639,630 | 6/1997 | Malin et al. | 435/28 |

OTHER PUBLICATIONS

Technicon H·3 RTX™ System Reference Guide, Jun. 1993, Publication No. TK9–2823–10, pp. 4–15; 4–17/18.

M.J. Malin et al., 1989, "Evaluation of 24–Second Cyanide––Containing and Cyanide–Free Methods for Whole Blood Hemoglobin on the Technicon H*1™ Analyzer with Normal and Abnormal Blood Samples"; *American Journal of Clinical Pathology*, vol. 92, No. 3, pp. 286–294.

M.J. Malin and S.S. Fan, 1992, "Mechanism of automated alkaline methods for the determination of hemoglobin in whole blood based on the micellization of ligated heme in the presence and absence of cyanide"; *Analytica Chimica Acta*, 262:61–77.

T. Matsubara et al., 1972, "Proposal for an Improved Reagent in the Hemiglobincyanide Method"; *Modern Concepts in Hematology*, pp. 29–43.

B.A. Payne et al., 1986, "Evaluation of the TOA E–5000® Automated Hematology Analyzer"; Dept. of Laboratory Medicine, Mayo Clinic and May Foundation, Rochester, Minnesota, pp. 51–57.

D. Seigneurin et al., 1983, "Interference of Hyperleukocytosis on Coulter Counter Model S Blood Counts: Methods for Correction"; *Biomedicine & Pharmacotherapy*, 37, pp. 401–404.

*Primary Examiner*—Maureen M. Wallenhorst
*Attorney, Agent, or Firm*—Morgan & Finnegan, L.L.P.

[57] ABSTRACT

The invention describes an improved stable reagent composition and method for the determination of hemoglobin (Hb) using whole blood samples and automated hematology analyzers. The Hb reagent contains an inorganic cyanide salt, at least one surfactant and a base and has a final pH of about 10.0 to about 11.2, preferably about 10.4 to about 11.2 or less and more preferably about 10.8 to about 11.2 or less. This reagent is intended for use as a universal Hb determination reagent for all of the instruments in the aforementioned series and will provide accurate and precise results without accompanying interference from elevated numbers of white blood cells, especially as found in abnormal blood specimens, and without system-to-system variation in the results obtained.

45 Claims, No Drawings

5,858,794

CYANIDE-CONTAINING HEMOGLOBIN REAGENT COMPOSITION AND METHOD PROVIDING ACCEPTABLE PRECISION, ACCURACY AND FREEDOM FROM WHITE CELL INTERFERENCE ON AUTOMATED HEMATOLOGY ANALYZERS

FIELD OF THE INVENTION

The invention relates to methods and reagent compositions used in the analysis of blood samples on semi-automated and automated hematology analyzers. More particularly, the invention relates to an improved cyanide-containing method is and reagent composition for the determination of hemoglobin in whole blood samples.

BACKGROUND OF THE INVENTION

The measurement of whole blood hemoglobin (Hb) is frequently performed using manual spectrophotometric methods and using semi-automated and automated hematology analyzers and methods and reagents used therein. Recent advances in high-throughput (e.g., up to about 100 samples per hour) hematology analyzers, e.g., the TECHNICON H●™ series, including, but not limited to, the TECHNICON H●1™, H●2™ and H●3™ systems have led to the need for Hb methods that reach completion in about 30 seconds or less.

Cyanide-containing and cyanide-free Hb methods and reagents are used in automated Hb analyzers, such as the TECHNICON H●™ series of instruments, to rapidly and quantitatively convert any carboxyhemoglobin (HbCO) in blood samples to a quantifiable reaction product, for example, in less than about 24 seconds. It has been found that Hb assays performed using either automated analyzers, for example, the TECHNICON H●™ series of hematology analyzers, are not affected by the presence of up to 100% HbCO as a percentage of total blood hemoglobin. In addition, it has been found that both cyanide-containing and cyanide-free methods performed using automated TECHNICON H●™ analyzers were comparable with respect to the performance parameters of linearity, precision and carry-over. Further, these methods correlated well with the International Committee for Standardization of Hematology (ICSH) Manual Reference Hb Method on normal and abnormal blood samples, thus indicating acceptable accuracy (M. J. Malin et al., 1989, *Am. J. Clin. Path.*, 92:286–294; M. J. Malin et al. 1992, *Analyt. Chim. Acta*, 262:67–77).

With regard to the analysis of abnormal blood samples which may contain aberrantly high levels of cells, particularly white blood cells, it may be difficult for current Hb determination methods and the reagents used therein to provide accurate and precise values. According to Wintrobe et al. (1981, *Clinical Hematology*, Lea and Febiger, Philadelphia, Pa., p. 208), a normal white blood cell count is on the order of about 3 to $10 \times 10^3$ cells/μl of blood. Thus, a moderately high normal count can be considered to be, for example, about $8 \times 10^3$ cells/μl, and an abnormally elevated white blood cell count can be considered to be about $10 \times 10^3$ cells/μl or greater.

U.S. Pat. No. 3,874,852 to T. E. Hammill discloses a reagent for the determination of leukocytes and hemoglobin in blood comprising a ferricyanide ion-free solution containing a quaternary ammonium ionic surfactant and an inorganic cyanide salt in which the pH of the reagent is approximately 9 and the pH of the final buffered solution used for analysis is 7.6 when employed with the commercial buffered blood diluent Isoton®.

Cyanide-containing hemoglobin reagents having a reagent pH in the range of from 11.2 to 11.5 or 11.6 are commerically available from the assignee hereof. However, as described herein, unexpected problems in Hb determinations using the available Hb reagents having particular pH values were not solved until the present inventor's discovery of the causes of the problems and the development of reagent compositions and methods in accordance with the present invention.

Accordingly, needed in the art are methods and reagents which eliminate interference caused by moderate to high white blood cell counts and which yield acceptable imprecision in the determination of hemoglobin. Also needed are methods and reagents which do not suffer from system-to-system variation and which are capable of accurately quantifying Hb content in situations of both moderately to highly elevated white blood cell counts in normal or abnormal blood samples.

Another problem in the art arises when a blood sample remains mixed with a Hb reagent composition in a reaction mixture for some time prior to Hb analysis. Differences in reaction rates of Hb methods can depend on the mechanistic aspects of the blood in the reaction mixture with the Hb reagent. For example, a large increase in the reaction rate of an automated method compared with the ICSH method can depend on the disruption of the Hb molecule and the extraction of a ligated hemin derivative by surfactant micelles in the former method. By contrast, in the ICSH method, the integrity of the Hb molecular structure is maintained and the oxidation of heme iron and the subsequent ligation by cyanide occurs within the intact Hb structure (M. J. Malin et al., 1989, *Am. J. Clin. Path.*, 92:286–294; M. J. Malin et al., 1992, *Analyt. Chim. Acta*, 262:67–77). For these reasons among others, current Hb determination reagents and methods used for particular automated instrumentation, such as the TECHNICON H●™ series of analyzers, may not always perform optimally under conditions of high white blood cell counts. In such cases, new reagents need to be developed and used by those in the art to avoid measurement imprecision and variation in results among different instruments or different instruments in a series, such as the TECHNICON H●™ analyzer series.

In view of the popular clinical utilization of whole blood Hb measurement and for the reasons presented hereinabove, those in the art are attuned both to maintaining the precision and accuracy of these spectrophotometric-based assays and to improving upon the analysis conditions and reagent compositions used in Hb determination methods. With respect to the reagent compositions for Hb analysis and measurement, ionic cyanide is still routinely used by those skilled in the art as a reagent component for Hb determination with effective, accurate and precise results. Needed in the art are methods and reagent compositions for Hb measurement and analysis that can be used with acceptable accuracy and precision in all types of hematology analyzers, for example, a cyanide-containing Hb method and reagent composition having superior performance capabilities in each of the TECHNICON H●™ series of analyzers with little to no system-to-system variation. The reagent compositions should optimally be formulated so that all of the specified features and components of such reagents, including the specifications for pH, cyanide, total alkalinity, surfactant concentration, osmolality and surface tension, provide precise results for the analysis of both normal and abnormal blood samples, which may contain both normal and unusually high levels of white blood cells.

SUMMARY OF THE INVENTION

Accordingly, it is an object of the present invention to provide an improved method and stable reagent composition for providing Hb measurement and determination in whole blood. In accordance with the invention, such a method and composition comprise a cyanide-containing reagent that can be universally employed in the various types of Hb analyzers, particularly, in the TECHNICON H●™ series of automated systems, for the spectrophotometric determination of Hb in both normal and abnormal blood samples.

Another object of the present invention is to provide a method and reagent composition employed therein for obtaining precise Hb determinations using whole blood samples having a normal white blood cell count, as well as blood samples having elevated and abnormally high levels of white blood cells, such as on the order of at least approximately $8 \times 10^3$ white blood cells/μL or greater. Indeed, the composition and method of the present invention can provide accurate Hb values for blood samples having at least about $60 \times 10^3$ white blood cells per microliter.

Yet another object of the present invention is to provide a cyanide-containing Hb reagent composition which comprises the above-described specified reagent features and a reagent pH that avoids unacceptable imprecision in results, particularly in the analysis of blood samples having high white blood cell counts. More particularly, the reagent compositions of the invention comprise a pH in the range of about 10.0 to about 11.2, preferably in the range of about 10.4 to about 11.2, more preferably in the range of about 10.8 to less than 11.2. Such reagents afford precise Hb measurements on all blood samples analyzed and alleviates problems of system-to-system variation in carrying out such determinations. In the methods of the invention, the above-described reagent is reacted with a blood sample to form an aqueous reaction mixture for the determination of hemoglobin in the blood.

Further objects and advantages afforded by the invention will be apparent from the detailed description hereinbelow.

DETAILED DESCRIPTION OF THE INVENTION

The present invention provides an improvement in methods and reagents used to perform precise Hb determinations using normal and abnormal whole blood samples. The particular method and reagent of the invention are suitable for use with both semi-automated and fully-automated hematology spectrophotometric analyzers. Particularly preferred for use are hemoglobin analyzer systems available from the assignee hereof, including but not limited to, the TECHNICON H●™ series of hematology analyzers. Sample fluids on which such determinations are performed include fresh whole blood, aged or stored blood (for example, about 54 hours), manipulated test samples and specially-prepared controls and calibrators derived from whole blood used to test the performance of and/or calibrate hematology analyzers.

The development of the improved Hb determination method and reagent composition in accordance with the present invention stemmed from an unexpected lack of precision in the results obtained using currently-available cyanide-containing Hb reagents in automated methods to analyze blood samples having moderately to abnormally elevated numbers of white blood cells. Inaccuracies and unacceptable imprecision were particularly and unexpectedly noticed when performing Hb measurement analyses on blood samples having a minimum white blood cell count of at least approximately $8 \times 10^3$ cells/μL and using a commercially-available cyanide-containing Hb reagent having a reagent pH of about 11.5–11.6. Imprecision was also observed using automated analyzers, e.g., the TECHNICON H●™ hematology instrument series, in which a blood sample was mixed with the Hb reagent for a time (e.g., about 30 seconds) to form a reaction mixture prior to Hb analysis by the automated system. The resultant unacceptable imprecision was determined to be a consequence of white blood cell interference in the blood sample, and was not attributed to the platelet component. Example 4 shows that white blood cells and not platelets were the cause of the interference in Hb measurement.

It was found by the present inventor that the presence of a high number of white blood cells in a blood sample led to interference in the Hb channel of the instrument, thereby skewing the Hb determination results. Tables 1 and 2 present data illustrating the random and erratic results obtained for one blood sample analyzed (10 replicates each) with the cyanide-containing Hb reagent with a pH of 11.6 (Table 1) versus the same blood sample analyzed with the Hb reagent after the pH was manipulated to 11.2 by addition of HCl (Table 2).

TABLE 1

Ten Replicate Analyses of One Blood Sample: Hb Reagent pH 11.6

| Replicate Number | WBCP[1] | RBC | Hb | MCV[2] | PLT | MPV[3] | WBCB[4] | HCT[5] |
|---|---|---|---|---|---|---|---|---|
| 1 | 26.90 | 5.69 | 15.4 | 81.7 | 772 | 8.6 | 26.59 | 46.5 |
| 2 | 27.07 | 5.69 | 15.2 | 81.4 | 764 | 8.6 | 26.90 | 46.3 |
| 3 | 27.28 | 5.77 | 16.0 | 81.5 | 765 | 8.5 | 27.46 | 47.1 |
| 4 | 26.82 | 5.68 | 15.1 | 81.3 | 786 | 8.5 | 27.76 | 46.2 |
| 5 | 26.09 | 5.73 | 16.4 | 81.3 | 778 | 8.4 | 27.73 | 46.6 |
| 6 | 26.35 | 5.77 | 15.0 | 81.5 | 782 | 8.6 | 28.42 | 47.0 |
| 7 | 27.11 | 5.61 | 15.1 | 81.4 | 786 | 8.6 | 27.30 | 45.7 |
| 8 | 26.20 | 5.66 | 15.4 | 81.2 | 764 | 8.5 | 27.74 | 45.9 |
| 9 | 26.74 | 5.66 | 15.8 | 81.5 | 773 | 8.5 | 28.64 | 46.2 |
| 10 | 26.23 | 5.77 | 15.7 | 81.5 | 775 | 8.4 | 28.79 | 47.0 |
| Mean | 26.76 | 5.70 | 15.5 | 81.4 | 775 | 8.5 | 27.73 | 46.5 |

TABLE 1-continued

Ten Replicate Analyses of One Blood Sample: Hb Reagent pH 11.6

| Replicate Number | WBCP[1] | RBC | Hb | MCV[2] | PLT | MPV[3] | WBCB[4] | HCT[5] |
|---|---|---|---|---|---|---|---|---|
| S.D. | 0.379 | 0.055 | 0.46* | 0.14 | 8.5 | 0.08 | 0.721 | 0.48 |
| C.V. | 1.4 | 1.0 | 2.9* | 0.2 | 1.1 | 0.9 | 2.6 | 1.0 |

*exceeded specification
[1]WBCP: White blood cell count from the peroxidase channel
[2]MCV: Mean red blood cell volume
[3]MPV: Mean platelet volume
[4]WBCB: White blood cell count from the basophil channel
[5]HCT: Hematocrit

TABLE 2

Ten Replicate Analyses of One Blood Sample: Hb Reagent pH 11.2

| Replicate Number | WBCP[1] | RBC | Hb | MCV | PLT | MPV | WBCB[2] | HCT |
|---|---|---|---|---|---|---|---|---|
| 1 | 26.79 | 5.72 | 15.1 | 81.5 | 755 | 8.4 | 27.47 | 46.6 |
| 2 | 26.51 | 5.73 | 15.1 | 81.3 | 733 | 8.4 | 27.67 | 46.6 |
| 3 | 26.53 | 5.70 | 14.8 | 81.1 | 752 | 8.4 | 27.62 | 46.3 |
| 4 | 26.70 | 5.70 | 15.1 | 80.9 | 745 | 8.4 | 27.65 | 46.2 |
| 5 | 26.44 | 5.75 | 14.9 | 80.8 | 782 | 8.3 | 27.66 | 46.4 |
| 6 | 26.67 | 5.76 | 15.0 | 80.6 | 751 | 8.3 | 27.27 | 46.4 |
| 7 | 26.62 | 5.72 | 15.3 | 80.5 | 765 | 8.3 | 28.06 | 46.1 |
| 8 | 26.40 | 5.79 | 15.0 | 80.6 | 749 | 8.3 | 27.62 | 46.7 |
| 9 | 27.05 | 5.84 | 15.2 | 81.0 | 777 | 8.4 | 28.79 | 47.3 |
| 10 | 27.09 | 5.77 | 15.0 | 80.9 | 764 | 8.3 | 28.27 | 46.7 |
| Mean | 26.69 | 5.75 | 15.1 | 80.9 | 757 | 8.4 | 27.81 | 46.5 |
| S.D. | 0.232 | 0.044 | 0.14 | 0.32 | 14.9 | 0.05 | 0.445 | 0.34 |
| C.V. | 0.9 | 0.8 | 1.0 | 0.4 | 2.0 | 0.6 | 1.6 | 0.7 |

[1]White blood cell count from the peroxidase channel
[2]White blood cell count from the basophil channel There is unacceptable variation in the Hb replicates as shown in Table 1. For example, replicates 3 and 5 are high "outliers". Two or three such outliers were typically obtained with a blood sample containing >8×10³ WBC/μl and a Hb reagent with pH 11.6. In contrast, the Hb data shown in Table 2 has acceptable imprecision; the occurrence of high outliers was prevented by manipulation of the Hb reagent pH to 11.2.

More particularly, in several of the TECHNICON H●™ analyzer systems tested, the presence of "particulates" in the Hb reagent-blood reaction mixture was detected in the basophil direct cytometry (Baso DC) channel because of differential light scattering caused by the presence of the particulates, compared with the bulk reaction mixture. The basophil channel was utilized in the DC mode to detect and aid in describing the nature of the interference problem in the Hb determination method. Because the basophil channel detects cytoplasm-stripped nuclei of all leukocytes (except basophils), the observation of detectable events with the use of basophil DC channel suggests that interference contributed to the Hb method by WBCs is related to their nuclei. As those skilled in the art will appreciate, among the blood cell populations, WBCs possess nuclei (and DNA), while RBCs and PLTs do not.

With specific regard to Baso direct cytometry, H●™ hematology analyzer systems contain a Baso channel in which white blood cells are analyzed (see U.S. Pat. No. 5,518,928 to J. F. Cremins et al.). In the Baso channel, blood cells are mixed with a reagent which lyses red blood cells and strips the cytoplasm of all white blood cells except for basophils. Hence, the majority of the white blood cells are detected as nuclei. In the present analysis, blood samples were manually diluted approximately 60-fold in the Hb reagent composition and then were mixed. The resulting reaction mixture was introduced into the Baso channel via the direct cytometry (DC) aspiration mode. Each reaction mixture was aspirated in this way for a total of four times, about 30 seconds apart. Thereafter, the mean +/−SD of the valid cell counts was tabulated.

Without wishing to be bound by a particular theory, the contaminating particulates could be DNA-based aggregates which absorb or scatter light differently from the bulk of the sample, thereby causing interference. As these aggregates are not likely to be distributed homogeneously in the Hb reaction mixture, their position in the flow cell with respect to the light path is different in each reaction mixture. Thus, in the Hb channel, in a set of ten aspirations, there was frequently only a very small number (e.g., 2–4) of strong outliers (see Table 1, replicates 3 and 5), which represent high outliers in the data set presented. By contrast, in the Baso DC channel, the action of flow allowed a much larger volume of reaction mixture to be viewed by the detector such that every reaction mixture containing a reagent composition having a pH of about 11.6 and a WBC count of $\geq 8 \times 10^3$ cells/μl of blood (i.e., a high buffy coat) yielded a valid count of 1250 "events" (Table 7). However, for a Hb reagent composition having a pH of less than about 11.5 or 11.6, or a pH of 11.6 with a low buffy coat sample, the valid count was 23 to 129 events. As used herein, buffy coat refers to white blood cells and platelets.

To achieve acceptable imprecision values (i.e., within statistical specification limits) in carrying out a Hb determination on blood samples of all types, including those having a white cell count of from about 8–35×10³ cells/μL or greater, an improved reagent composition was developed and used in the Hb methods. The reagent composition achieved in accordance with the present invention is an aqueous solution comprising an inorganic cyanide salt and having a reagent pH in the range of about 10.0 to about 11.2, preferably about 10.4 to about 11.2 and more preferably about 10.8 to less than 11.2. More preferred is a pH of the reagent composition of about 10.9 to about 11.1. An optimum pH range for the reagent composition of the present invention is greater than about 10.8 and less than about 11.2. For example, a pH of about 11.0 is particularly suitable. When reagents were prepared and tested having a reagent pH in the range of 10.8 to 11.2, these reagents afforded acceptable imprecision over the entire pH range as tested in 0.2 pH increments using an automated TECHNICON H●™ hematology analyzer (see Example 6).

The improved cyanide-containing reagent composition, having a distinct and different pH optimum from that of other Hb reagent compositions currently employed in Hb methods performed on the TECHNICON H●™ series of instruments, alleviated unacceptable imprecision data with high buffy coat blood samples and provided a stable reagent for Hb determinations. The reagent composition of the present invention is expected to have an enhanced shelf-life due to a lowering of the reagent pH (i.e., from about 11.4 or greater down to about 11.2 to about 10.4, preferably 11.2 or less to about 10.8). This is because cyanide is degraded by hydroxide ion, more of which are present in a reagent with a pH of 11.6 (Wiegand and Tremelling, 1972, *J. Org. Chem.*, 37:914). Examples 5 and 6 describe tests performed to evaluate the effect of reagent pH on the outcome of Hb determinations using whole blood samples.

The cyanide-containing Hb reagent composition of the present invention comprises the following components in aqueous admixture: an ionic surfactant, including cationic, anionic, or zwitterionic surfactants, or mixtures and combinations thereof; an ionic cyanide compound or cyanide salt to provide a cyanide ion and a suitable buffer to achieve and maintain the appropriate alkaline reagent pH in accordance with the present invention.

In the reagent composition of the present invention, the surfactant causes hemolysis of the red blood cells in the sample. In parallel, dissolution of cell debris and plasma lipids and the formation of micelles is also expected to occur due to the action of the surfactant component. At alkaline pH, the Hb structure loses most of its salt bridges. The Hb protein structure is further disrupted by exposure of the heme molecules to the components of the reagent composition.

Without wishing to be bound by theory, more particularly, the action of surfactant and the alkaline pH release the hemes from combination with globin to yield a mixture of ferric and ferrous hemes. The hemes are air-oxidized to ferric, the iron(III) state. Next, axial ligation and micellization of the ferric hemes occur to form specific end products identified by characteristic absorption spectra. The oxidation of heme iron and the ligation of heme iron by cyanide occur after the hemes have been released from the globin molecules. For the cyanide reaction, cyanides (2) bind to the hemes as axial ligands. Dicyanoiron(III)porphyrin is extracted into the dispersed micellar phase and assumes a position within the interior of the micelle (i.e., micellized dicyanoferriporphyrin) to generate a colored (i.e., red-brown) product. Further description of the biochemical mechanisms and functions of the components of cyanide-containing Kb reagents may be found in M. Malin et al., 1992, *Anal. Chim. Acta*, 262:77.

Those skilled in the art will appreciate that the cyanide ion, when introduced into a blood sample via mixing with the reagent composition, is optimally freely available to combine chemically with heme iron and is therefore not too tightly bound to its associated metal ion. In accordance with the present invention, the cyanide ion is supplied preferably in the form of a salt with an inorganic cation, especially an alkali metal cation, preferably a monovalent cation, such as sodium, lithium, potassium, or ammonium. Cyanide salts of polyvalent metal cations, e.g., divalent or trivalent metal cations, may be considered for use; however, such polyvalent ions may not allow cyanide to bind optimally to heme iron in the reaction mixture due to the strong binding of the polyvalent metal ion to cyanide. Further, di- and trivalent cations are known to form insoluble hydroxide precipitates which are unsuitable in the present invention. The inorganic cyanide salt is present in the composition at a concentration of about 0.5 to 5 g/l, preferably about 1 to 2 g/l.

The aqueous reagent composition solution of the present invention comprises the aforedescribed components dissolved in water and has a final reagent pH of from about 10.0 to about 11.2, preferably from about 10.4 to about 11.2, more preferably about 10.8 to less than 11.2, most preferably about 10.9 to about 11.1. An optimal pH of the reagent composition is about 11.0 in accordance with the present invention. One or more buffer components, in admixture, provide(s) the appropriate pH to the reagent composition. The present reagent composition is free of ferricyanide ion. The osmolality of the Hb reagent composition is about 450 to about 490 mosm/kg. The surface tension for the reagent composition of the invention is about 31–32 dynes/cm.

Examples of ionic surfactants suitable for use in the invention include, but are not limited to, zwitterionic, anionic and cationic surface active agents. With particular regard to zwitterionic surfactants, several general classes of these surfactants may be considered for use in the composition of the present invention. Examples of suitable classes of zwitterionic surfactants are betaines, including carboxy betaines, sulfobetaines (also known as sultaines), amidobetaines and sulfoamidobetaines. Of particular interest are the $C_8$–$C_{18}$, preferably $C_{10}$–$C_{18}$, alkyl betaines, sulfobetaines, amido betaines, and sulfoamido betaines, for example, those of the laurylamidopropylbetaine (LAB) type. Mixtures or combinations of surfactants may also be employed in the composition and method of the present invention.

Nonlimiting examples of suitable zwitterionic surfactants in the betaine class include n-alkyldimethylammonio methane carboxylate (DAMC), n-alkyldimethylammonio ethane carboxylate (DAEC) and n-alkyldimethylammonio propane carboxylate (DAPC). Examples of the sulfobetaine class of zwitterionic surfactants include, but are not limited to, the n-alkylsultaines, or n-alkyl dimethylammonio alkyl sulfonates, such as n-alkyl dimethylammonio methane sulfonate (DAMS), n-alkyl dimethylammonio ethane sulfonate (DAES), n-alkyl dimethylammonio propane sulfonate (DAPS) and n-alkyl dimethylammonio butane sulfonate (DABS). Of the DAPS surfactants, TDAPS, wherein "T" is n-tetradecyl; DDAPS, wherein "D" is dodecyl; as well as hexadecyl dimethylammonio propane sulfonate, are especially suitable.

The amidobetaines include, but are not limited to, n-alkylamidomethane dimethylammonio methane carboxylate or n-alkylamido methane dimethylammonio ethane carboxylate. A preferred amidobetaine is laurylamidopropylbetaine (LAB). Also suitable are the analogous amidobetaine sulfonates, such as n-alkylamidomethane dimethylammonio methane sulfonate, n-alkylamidoethane dimethylammonio ethane sulfonate and n-alkylamidopropane dimethylammonio propane sulfonate. In addition, amidobetaines which have coconut oil as their fatty acid source, e.g., cocoamidopropylbetaine (CAPB) and cocoamidosulfobetaine (CASB), may be considered for use. Further descriptions of betaines, sulfobetaines, amidobetaines and amidosulfobetaines may be found in the pertinent literature, for example, S. Takano et al., 1977, *J. Amer. Oil Chem. Soc.*, 54:139–143 and 484–486; Z. El Rossi, Cs Horvath, 1982, *Chromatographia*, 15:75–82; Kaminsid and Linfield, 1979, *J. Amer. Oil Chem. Soc.*, 56:771–773.

Other zwitterionic surfactants suitable for use in the invention include N,N-dimethyl laurylamine N-oxide (also known as DMLAO or LO), N,N-dimethyl myristylamine N-oxide, N,N-dimethyl cetylamine N-oxide and N,N-dimethyl stearylamine N-oxide. Also suitable for use are zwitterionic surfactants which include 3-[(3-cholamidopropyl) dimethylammonio]-1-propanesulfonate (CHAPS) and 3-[(3-cholamidopropyl)dimethylammonio]-2-hydroxy-1-propanesulfonate (CHAPSO).

Anionic surfactants that can be used include, but are not limited to, the alkali metal salts of the $C_{12}$–$C_{18}$ alkyl sulfates, for example, sodium lauryl sulfate, lithium lauryl sulfate, and sodium myristyl sulfate. In general, the ionic surfactant has a hydrocarbon chain of about 12–18 carbon atoms, usually unbranched, with one ionic head group. The head group can be cationic, anionic, or zwitterionic.

Other classes of ionic surfactants that may be considered for use in the invention include the alkyltrimethylammonium hydroxides, especially the long chain alkyltrimethylammonium hydroxides, such as stearyltrimethylammonium hydroxide, lauryltrimethylammonium hydroxide, myristyltrimethylammonium hydroxide and cetyltrimethylammonium hydroxide.

Another class of ionic surfactants includes the cationic quaternary ammonium halides, preferably the $C_{12}$–$C_{18}$ alkyltrimethylammonium halides. For example, the $C_{12}$–$C_{18}$ alkyl can be cetyl, stearyl, myristyl, or lauryl; the halide can be chloride or bromide or fluoride. CTAB or cetyltrimethylammonium bromide is an example. In general, the surfactant is present in the composition at a concentration of about 10 to 40 grams per liter (g/l), preferably about 15 to 25 g/l, and more preferably, about 20 g/l. Zwitterionic surfactants are preferred for use in the present invention.

Buffering systems (or buffers) for use in the present Hb reagent composition and method provide resistance against pH change of the reagent solution. Buffers conventionally used in the art and having the appropriate $pK_a$ values for maintaining reagent pH in the range of about 10.0 to about 11.2, preferably about 10.4 or greater to less than 11.2, more preferably about 10.8 to about 11.1, and most preferably, about 10.9 to about 11.1 can generally be employed in the Hb reagent composition of the present invention. An optimal pH of the reagent composition is about 11.0. Examples of suitable buffers include, but are not limited to, 3-[cyclohexylamino]-1-propanesulfonic acid (CAPS); borax (i.e., sodium tetraborate); carbonates, such as potassium, calcium or sodium carbonate and TRIS. Buffers are used in the composition of the invention at a concentration of about 0.05M to 0.15M, preferably about 0.075M to 0.125M, and more preferably about 0.10M. Preferred is a pH buffer system comprising borax (0.05M) and NaOH (0.1M) in which a blood sample is diluted 250-fold such that the final pH of the blood reagent reaction mixture is in an acceptable pH range for the composition of the present invention.

The reagent composition of the present invention can include alkalinity agents (bases) as necessary and appropriate with suitable buffers. Nonlimiting examples of suitable bases include alkali metal hydroxides, such as sodium hydroxide or potassium hydroxide. Also suitable for use are bases such as tetraalkylammonium hydroxide, in which the alkyl group can contain from 1–4 carbon atoms, for example, tetrabutylammonium hydroxide. The base is preferably present in the composition in an amount of about 0.05 to about 0.5 moles/L, preferably about 0.05 to 0.2 moles/L, and more preferably about 0.1 moles/L.

In general, the method of the invention involves mixing a blood sample with the reagent composition of the invention to form a reaction mixture. A reaction product derived from the reaction of the components of the reagent composition with a naturally occurring hemoglobin species in the blood sample (either whole blood or a calibrator or control material) is detected spectrophotometrically at 546 nm. Included among the naturally occurring hemoglobin species that can be measured using the method and reagent composition in accordance with the invention are deoxyhemoglobin, oxyhemoglobin, methemoglobin, fetal hemoglobin, carboxyhemoglobin and sickle cell hemoglobin. The blood sample is diluted about 250-fold (more specifically, 251-fold: 250 volumes of reagent plus 1 volume of blood sample) with the reagent composition and the resulting reaction product has a reproducible absorption spectrum with a maximum absorption at 549.5 nm (M. Malin et al., 1992, *Anal. Chim. Acta*, 262:67).

EXAMPLES

The following examples as set forth herein are meant to exemplify the various aspects of carrying out the invention and are not intended to limit the invention in any way.

The following abbreviations are used in the examples herein: BC: Buffy Coat; % CV: Coefficient of Variation; df: degrees of freedom; DC: Direct Cytometry; Hb: Hemoglobin; PLT: Platelet(s); PLT Count: PLT×$10^3$/µl; RBC: Red Blood Cell(s); RBC Count: RBC×$10^6$/µl; SD: Standard Deviation; WBC: White Blood Cell(s); WBC Count: WBC×$10^3$/µl; WBCB: White Blood Cell Count obtained from the basophil channel of an H●™ hematology system; WBCP: White Blood Cell Count obtained from the peroxidase channel of an H●™ hematology system.

EXAMPLE 1
Preparation of Normal and Specially Manipulated Blood Samples

In the experiments designed to test the performance of different Hb reagents and to measure and determine Hb and cell counts in various types of blood samples, whole blood was collected from volunteers at Bayer Corporation ("normal" blood samples) in Vacutainer® tubes, anticoagulated with EDTA (preferably $K_3$EDTA) and stored at room temperature. These normal blood samples were routinely used within 8 hours after collection. Whole blood was centrifuged at 2500 rpm (700×g) for 30 minutes to pack the buffy coat (defined as the white blood cells and platelets) on top of the red blood cells. Blood samples were also manipulated to achieve test samples having particular properties. For example, to manipulate the white blood cell count to about 15 to 20×$10^3$ cells/µL of blood, the buffy coats of two to three tubes were combined in one tube of the same donor's blood sample.

To prepare a manipulated blood sample having low WBC, high PLT and normal RBC, eight tubes of blood were centrifuged from a single donor at 2500 rpm for 25 minutes. The plasmas were transferred to clean tubes. The buffy coats were transferred to two Wintrobe hematocrit tubes and the tubes were centrifuged as above. The plasma layer and most of the PLT layer were transferred from the Wintrobe tube to a small clean test tube. 1 mL of plasma was added and the tube was centrifuged at 1000 rpm for 10 minutes. The supernatant was then decanted into a tube containing only RBC; plasma was added to the original volume and mixed.

To prepare a manipulated blood sample having high WBC, low PLT and normal RBC, the WBC layer was transferred from the Wintrobe tube to a tube containing only RBC. Plasma was added to the original volume and mixed.

EXAMPLE 2
Statistics: Validation of the Experimental Design Based on N=10

Tests to evaluate the performance of different lots of test Hb reagent compositions, particularly those having differences in reagent pH, in the Hb determination method generally contained three elements: a negative reagent control and a test reagent, both of which had to pass the specifications of the method performed on an automated analyzer, and a positive reagent control which had to fail the specifications. All data sets contained ten replicates. The specifications included SD and % CV.

As an illustrative example, for the purposes of the TECHNICON H●3™ system, there were two specifications for the Hb method, namely, 0.124 for SD and 0.78 for % CV. With this instrument, the SD specification was maintained until Hb=15.9 g/dL, i.e., [100 (0.124/0.78)=15.9]. At a value above 15.9 g/dL for SD, the % CV specification was controlling. That is, above 15.9 g/dL, it was possible to fail the SD specification, but to pass the % CV specification and obtain acceptable imprecision in the Hb determinations.

The CHI-SQUARE statistic was used to determine the sample SD which was significantly different from the specification, 0.124, based on a sample set of 10 replicates for sample Hb concentrations up to and including 15.9 g/dL. $[s^2/sigma^2] > CHI^2_{0.95}/df$, where $s^2$ is the sample variance; $sigma^2$ is the variance of a normal population; $CHI^2_{0.95}/df$ is the CHI-SQUARE statistic at 5% level of significance, $[s^2/(0.124)^2] > 1.88$ $s^2 > 1.88 (0.0154)$ $s > 0.170$, where s is the sample standard deviation.

Thus, for N=10 (and 9 df), if SD>0.17 for a particular data set, then this set was significantly different from the specification, SD=0.124 (Dixon and Massey, 1983, Introduction to Statistical Analysis, McGraw Hill, page 110). Accordingly, in each performance test with sample Hb concentrations up to and including 15.9 g/dL, the goal was to obtain a SD>0.17 with a positive reagent control. The positive reagent control demonstrated that the system was capable of responding to the problem of unacceptable imprecision values under the conditions of the test.

For sample Hb concentrations of greater than 15.9 g/dL, the % CV specification was employed to calculate the corresponding SD using the relationship, Hb in g/dL=(SD× 100)/0.78. The following Table 3 was generated and the CHI-SQUARE statistic was used to calculate the corresponding sample SD which would be significantly different from the specification.

TABLE 3

| Hb, g/dL | Specification SD | Sample SD That Is Significantly Different From Specification with N = 10 |
|---|---|---|
| 16.0 | 0.125 | 0.171 |
| 17.0 | 0.133 | 0.182 |
| 18.0 | 0.140 | 0.192 |
| 19.0 | 0.148 | 0.203 |
| 20.0 | 0.156 | 0.214 |
| 21.0 | 0.164 | 0.224 |
| 22.0 | 0.172 | 0.236 |
| 23.0 | 0.179 | 0.245 |
| 24.0 | 0.187 | 0.256 |
| 25.0 | 0.195 | 0.267 |

In these evaluations, decisions regarding the acceptable or unacceptable nature of a test reagent were based solely on the SD specification.

EXAMPLE 3

An illustrative Hb reagent composition prepared in accordance with the invention and used in the Hb determinations as described is presented in Table 4.

TABLE 4

| Reagent Component | Quantity/liter |
|---|---|
| Sodium Borate | 19.07 g |
| Base (Sodium Hydroxide) | 4.0 g |
| Surfactant (tauryl Dimethylamine Oxide, 30 g/100 mL in water) | 66 mL |
| Potassium Cyanide | 1.3–1.6 g |
| 10 N Sodium Hydroxide | 0.65 mL |
| 3 N Hydrochloric Acid | As Required |
| Deionized Water, qs to | 1 L |

The reagent composition was filtered after preparation using an 0.2 micron polysulfone or nylon membrane. The final pH of this illustrative reagent composition was 11.0 at 25°±3° C.; the total alkalinity was not less than 180 mEq/L; its appearance was a clear, colorless liquid which was essentially free of particulate matter upon visual inspection.

EXAMPLE 4

Determination that White Blood Cells and Not Platelets Are the Source of Interference in the Sample Buffy Coat Experiments were performed to assess whether white blood cells or platelets were the source of interference in the Hb analyses performed on the TECHNICON H●™ series of hematology analyzers. Cyanide-containing reagents were prepared and tested having the same ingredients and differing in reagent pH. Through these analyses, it was found that blood samples with high buffy coats (i.e., elevated both in WBC and PLT by manipulation) were associated with a large SD when used with a Hb reagent having a pH of 11.6, analyzed on the TECHNICON H●3™ system. Thus, evaluations were conducted to determine the effect on imprecision of high WBC or high PLT in the presence of a normal RBC count.

As presented in Table 5, WBC, and not PLT, were observed to be causal to the problem of imprecision in these analyses. For example, the SD was 0.22 when WBCP(high), PLT(low) were 26.25 and 71, respectively, (i.e., CHI-SQUARE was satisfied). Conversely, SD was 0.08 when WBCP(low), PLT(high) were 0.24, 938, respectively. It is noted that the fractionation process used to prepare the manipulated samples caused the high WBC sample to contain 93% neutrophils, which are therefore a cause of imprecision at pH 11.6. It is also likely that other types of WBCs, in addition to neutrophils, (i.e., lymphocytes, monocytes, basophils and eosinophils) would contribute to high levels of interference in the Hb determination assays.

TABLE 5

Test for Imprecision: WBC Versus PLT

| | Hb Test Reagent, pH 11.6 | | | | Sample | | CHI-SQ |
|---|---|---|---|---|---|---|---|
| Exp't | WBCP | RBC | PLT | Hb, g/dL | SD spec | % CV | SD |
| 1 | 0.09 | 4.99 | 3 | 15.8 | 0.07 | 0.4 | >0.17 |
| 2 | 24.27 | 5.78 | 835 | 18.3 | 0.27* | 1.5 | >0.203 |
| 3 | 2.79 | 4.78 | 836 | 15.1 | 0.08 | 0.5 | >0.17 |
| 4 | 0.24 | 5.14 | 938 | 16.3 | 0.08 | 0.5 | >0.182 |
| 5 | 26.25 | 4.95 | 71 | 15.6 | 0.22* | 1.4 | >0.17 |

All of these samples were manipulated as described in Example 1.
*Failed specification

EXAMPLE 5

Experiments Showing that Reagent pH is Directly Linked to Imprecision of Hb Assay Results To ascertain whether or not reagent pH was a causal factor in producing acceptable imprecision values in the Hb assays, Hb reagents were prepared in which the reagent pH was manipulated from a pH value of 11.42 to a pH of 11.66. Other test reagents were prepared in which the reagent pH was manipulated from 11.60 to 10.8 or to 11.2 or to 11.3. As described herein, it was determined that reagents with a pH of above about 11.5 to about 11.6 (or higher, e.g., 11.66) produced unacceptable imprecision in the Hb determinations of samples having high WBC counts. The experiments were designed to discover if changing the pH of a given Hb reagent could convert that reagent to one which provided acceptable imprecision values in the Hb analyses performed on the H●™ hematology analyzer system. The various Hb reagents so prepared were assayed with blood samples in the H●™ automated hematology analyzer and were assigned a "pass" or "fail" criterion, depending on whether acceptable imprecision ("pass") or unacceptable imprecision ("fail") resulted from the Hb measurement obtained. The blood sample set used in these experiments included a high buffy coat sample (i.e., WBCP:RBC:PLT=19.76:6.37:704) and a low buffy coat sample (i.e., WBCP:RBC:PLT= 0.66:4.98:14). The results of these tests are presented in Table 6.

TABLE 6

Effect of pH Manipulation on Performance of Test Hb Reagents Using TECHNICON H● ™ Hematology Instrumentation

| Reagent | pH | Sample Buffy Coat | Hb, g/dl/L | SD | % CV | P/F |
|---|---|---|---|---|---|---|
| Reagent 1 | 11.42 | high | 18.3 | 0.10 | 0.50 | P |
|  | 11.66 | high | 18.5 | 0.38* | 2.00 | F |
| Reagent 1 | 11.66 | low | 14.1 | 0.11 | 0.80 | P |
| Reagent 2 | 11.60 | high | 18.3 | 0.27* | 1.50 | F |
|  | 11.17 | high | 18.2 | 0.11 | 0.60 | P |
| Reagent 3 | 11.56 | high | 18.8 | 0.44* | 2.30 | F |
|  | 11.29 | high | 18.3 | 0.10 | 0.60 | P |
| Reagent 2** | 10.80 | high | 18.3 | 0.07 | 0.40 | P |
|  | 11.66 | high | 18.9 | 0.68* | 3.60 | F |
| Specification | 11.2–11.6 |  |  |  |  |  |

|  | Sample SD spec | CHI-SQUARE SD |
|---|---|---|
| high buffy coat: WBCP:RBC:PLT = 19.76:6.37:704 | 0.148 | >0.203 |
| low buffy coat: WBCP:RBC:PLT = 0.66:4.98:14 | 0.124 | >0.170 |

*Failed specification
**In this aspect of the experiment, th pH of Reagent 2 (pH 10.8) was lowered to 10.8 from a higher reagent pH (i.e., 11.66) by the addition of 5 mM EDTA (i.e., Na$_2$EDTA). In the case of Reagent 2 (pH 11.66), the pH was adjusted back to 11.66 following the addition of 5 mM EDTA.

The results from these studies demonstrated that pH was a significant factor for Hb reagents having a pH of 11.6 and above as used in the automated Hb determination method. By contrast, Hb reagents having a pH from about 10.8 to 11.4 passed the test. A preferred pH range for the composition and method of the present invention, i.e., about 10.4 to about 11.2 or less, more preferably about 10.8 to about 11.2 or less, was selected so that a "safety" zone (i.e., pH 11.3–11.5) was effectively placed between the top of the new specification and the pH associated with failure of the method (i.e., a pH greater than or equal to about 11.6). The creation of the safety zone allowed for small errors in the pH analysis.

As seen from the results presented in Table 6, the SD of the test Hb reagents which produced unacceptable imprecision improved from values of 0.27 and 0.44 to values of 0.11 and 0.10 following a lowering of the reagent pH to arrive at a Hb reagent having a pH range in accordance with the present invention. By contrast, for a reagent having a pH of 11.66, the SD deteriorated, i.e., from 0.10 to 0.38, after the reagent pH was increased. CHI-SQUARE was satisfied in all cases in which the reagent pH≧11.6 and the sample contained a high buffy coat concentration (WBC and PLT).

EXAMPLE 6 pH Variation and Precision of the Hb Method

Additional experiments were carried out to assess the effects on the imprecision of the data obtained after varying the pH of the Hb reagent and method. A set of Hb reagents was prepared in which the reagent pH was adjusted with 6N HCl in 0.2 pH increments to generate a pH variation series having reagent pHs of 11.6, 11.4, 11.2, 11.0, 10.8, 10.6 and 10.4. Imprecision was evaluated over the pH range of 10.4 to 11.6 in order to determine if there was a minimum imprecision within the range. All of the reagents in the pH variation series were tested with a high buffy coat sample, i.e., WBCP:RBC:PLT=26.76:5.70:775. The pH 11.6 reagent was also tested with a low buffy coat sample as a control. Whether or not a given reagent provided performance results with acceptable imprecision (pass) or unacceptable imprecision (fail) was based on the use of the CHI-SQUARE statistic in conjunction with the current specifications. SD was used as the pass/fail criterion in all assays performed.

The data from these experiments are presented in Table 7. The data show that Hb reagents prepared in accordance with the invention and having a reagent pH of from about 10.4 to 11.4 had acceptable imprecision in the method, even with a high buffy coat blood sample. Additional testing indicated that a reagent pH of from about 10.0 to about 10.4 is also able to provide acceptable imprecision in the Hb method. By contrast, unacceptable imprecision was shown by the reagent having a pH of 11.6 with the high buffy coat sample. A sample size of ten was too small to allow a statistically valid discrimination among the SDs in the pH range of 10.4 to 11.4 with respect to the identification of a possible minimum SD. However, a visual inspection of the resulting SDs indicated an imprecision minimum at a pH of about 11.0. This was also supported by the Baso DC data which showed a minimum valid cell count at pH 11.0.

In Table 7, the "N control" and "H control" samples represent normal control and high control material. In-date Test Point™ Hematology Control Material was obtained from Bayer Corporation, Business Group Diagnostics, Tarrytown, N.Y. The numbers are the labeled ranges expected for these parameters.

These results demonstrate that acceptable imprecision was obtained with the Hb reagent composition (Table 4) over the pH range of about 10.4 to about 11.2. Unacceptable imprecision was obtained at pH 11.6. All of the tests were performed with a manipulated blood sample which contained $26.76 \times 10^3$ WBC/$\mu$l. On the basis of both the Hb analyses and Baso DC, minimum imprecision in the Hb determination is found with an Hb reagent composition having a pH of about 11.0 (in the broader range of about 10.0 to about 11.2 or less).

TABLE 7

Effect on imprecision of Test Hb Reagents Due to pH Variation from 11.6 to 10.4

| Reagent | pH | Sample | Hb, g/dL | SD | % CV | P/F | Baso DC: Valid Counts |
|---|---|---|---|---|---|---|---|
| Test Reagent 1 | 11.40 | Whole Blood | 14.2 | 0.07 | 0.50 | P | |
| | | N control | 13.5 | 0.06 | 0.40 | P | |
| | | H control | 18.5 | 0.06 | 0.30 | P | |
| Test Reagent 2 | 11.60 | HI buffy | 15.5 | 0.46* | 2.90 | F | 1250 +/− 1520 |
| | 11.60 | LO buffy | 14.1 | 0.11 | 0.80 | P | 25 +/− 3 |
| | 11.40 | HI buffy | 15.0 | 0.09 | 0.60 | P | 92 +/− 122 |
| | 11.20 | HI buffy | 15.0 | 0.09 | 0.60 | P | 29 +/− 7 |
| | 11.00 | HI buffy | 15.0 | 0.05 | 0.30 | P | 23 +/− 15 |
| | 10.80 | HI buffy | 15.0 | 0.07 | 0.50 | P | 55 +/− 38 |
| | 10.60 | HI buffy | 15.1 | 0.11 | 0.70 | P | 77 +/− 10 |
| | 10.40 | HI buffy | 15.0 | 0.09 | 0.60 | P | 129 +/− 50 |
| Mean | | | | +0.12 | +0.8 | | |

| | WBCP | RBC | PLT | Hb | Sample SD | CHI-SQUARE SD |
|---|---|---|---|---|---|---|
| N control | 7.42 +/− 0.85 | 4.48 +/− 0.2 | 212 +/−30 | 13.2 +/− 0.5 | | |
| H control | 18.43 +/− 2.5 | 5.53 +/− 0.3 | 450 +/−60 | 17.9 +/− 0.7 | | |
| Whole Blood | 10.90 | 5.36 | 327 | 14.2 | 0.124 | >0.17 |
| High buffy coat | 26.76 | 5.70 | 775 | 15.5 | 0.124 | >0.17 |
| Low buffy coat | 0.80 | 5.35 | 19 | 14.1 | 0.124 | >0.17 |

Specification;
*exceeded specification; all N = 10

The contents of all patents, patent applications, published articles, books, references, manuals, and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A reagent composition for determining hemoglobin in a whole blood sample, comprising an aqueous reagent solution containing at least one surfactant, an inorganic cyanide salt, and a pH buffer for maintaining a pH of the reagent composition at about 10.4 to less than about 11.2.

2. The composition according to claim 1, wherein the pH of the reagent composition is about 10.8 to about 11.1.

3. The composition according to claim 1, wherein the reagent composition pH is about 10.9 to about 11.1.

4. The composition according to claim 1, wherein the reagent composition pH is about 11.0.

5. The composition according to claim 1, wherein said reagent composition in admixture with a blood sample provides freedom from white blood cell interference and acceptable imprecision values in automated hemoglobin detection methods.

6. The composition according to claim 1, wherein the at least one surfactant is capable of lysing red blood cell membranes, suspending cell debris and forming micelles after mixing with a blood sample.

7. The composition according to claim 1, wherein the at least one surfactant is an anionic, cationic or zwitterionic surfactant.

8. The composition according to claim 7, wherein the zwitterionic surfactant is a $C_8$–$C_{18}$ alkyl betane, an alkyl sulfobetaine, an alkylamido betaine, an alkylamido sulfobetaine, or combinations thereof.

9. The composition according to claim 7, wherein the zwitterionic surfactant is selected from the group consisting of n-alkyldimethylammonio methane carboxylate (DAMC), n-alkyldimethylammonio ethane carboxylate (DAEC), n-alkyldimethylammonio propane carboxylate (DAPC), n-alkyl dimethylammonio methane sulfonate (DAMS), n-alkyl dimethylammonio ethane sulfonate (DAES), n-alkyl dimethylammonio propane sulfonate (DAPS), n-tetradecyl dimethylammonio propane sulfonate (TDAPS), n-tetradecyl dimethylammonio propane sulfonate (DDAPS), n-hexadecyl dimethylammonio propane sulfonate, n-alkyl dimethylammonio butane sulfonate (DABS), n-alkylamidomethane dimethylammonio methane carboxylate, n-alkylamido methane dimethylammonio ethane carboxylate, cocoamidopropylbetaine (CAPB), cocoamidosulfobetaine (CASB), laurylamidopropylbetaine (LAB), n-alkylamidomethane dimethylammonio methane sulfonate, n-alkylamidoethane dimethylammonio ethane sulfonate and n-alkylamidopropane dimethylammonio propane sulfonate.

10. The composition according to claim 7, wherein the zwitterionic surfactant is selected from the group consisting of N,N-dimethyl laurylamine N-oxide (DMLAO), N,N-dimethyl myristylamine N-oxide, N,N-dimethyl cetylamine N-oxide, N,N-dimethyl stearylamine N-oxide, 3-[(3-cholamidopropyl) dimethylammonio]-1-propanesulfonate (CHAPS) and 3-[(3-cholamidopropyl)-dimethylammonio]-2-hydroxy-1-propanesulfonate (CHAPSO).

11. The composition according to claim 1, wherein the at least one surfactant is selected from the group consisting of alkyltrimethylammonium hydroxides, cationic quaternary ammonium halides, and alkali metal salts of $C_{12}$–$C_{18}$ alkyl sulfates.

12. The composition according to claim 11, wherein the at least one surfactant is selected from the group consisting of stearyltrimethylammonium hydroxide, lauryltrimethylammonium hydroxide, cetyltrimethylammonium hydroxide, myristyl-trimethylammonium hydroxide, sodium lauryl sulfate, lithium lauryl sulfate and sodium myristyl sulfate.

13. The composition according to claim 1, wherein the at least one surfactant is present at a concentration of about 10 to 40 grams per liter.

14. The composition according to claim 1, wherein the pH buffer is selected from the group consisting of 3-[cyclohexylamino]-1-propanesulfonic acid (CAPS), sodium borate, potassium carbonate, calcium carbonate and sodium carbonate.

15. The composition according to claim 1, wherein the pH buffer is present in the composition at a concentration of about 0.05 to 0.15M.

16. The composition according to claim 1, further comprising a base, said base being an alkali metal hydroxide or a tetraalkylammonium hydroxide having an alkyl group with from 1–4 carbon atoms.

17. The composition according to claim 16, wherein the base is selected from the group consisting of sodium hydroxide, potassium hydroxide and tetrabutylammonium hydroxide.

18. The composition according to claim 16, wherein the base is present at a concentration of about 0.05 to 0.5 moles per liter and the cyanide salt is present at a concentration of about 0.5 to 5 grams per liter.

19. The composition according to claim 1, wherein the inorganic cyanide salt is capable of ligating to heme molecules released from globin after red cell lysis.

20. The composition according to claim 1, wherein the inorganic cyanide salt is selected from the group consisting of potassium cyanide, sodium cyanide, lithium cyanide and ammonium cyanide.

21. The composition according to claim 1, said composition having an osmolality of about 450 to about 490 mosm/kg.

22. A reagent composition for the determination of hemoglobin in a blood sample, comprising in aqueous admixture at least one surfactant in an amount effective to hemolyze red blood cells in a blood sample and form micelles; a soluble inorganic cyanide salt in an amount effective to bind to heme molecules resulting from said red blood cell hemolysis; and a pH buffer capable of maintaining a pH of said reagent composition at about 10.4 to less than about 11.2; wherein said reagent composition in admixture with a blood sample provides freedom from white blood cell interference in automated hemoglobin detection methods.

23. The composition according to claim 22, wherein the reagent composition pH is about 10.8 to about 11.1.

24. The composition according to claim 22, wherein the reagent composition pH is about 11.0.

25. The composition according to claim 22, wherein the at least one surfactant is a zwitterionic surfactant selected from the group consisting of $C_8$–$C_{18}$ alkyl betaines, alkyl sulfobetaines, alkylamido betaines and alkylamido sulfobetaines.

26. The composition according to claim 25, wherein the zwitterionic surfactant is selected from the group consisting of n-alkyldimethylammonio methane carboxylate (DAMC), n-alkyldimethylammonio ethane carboxylate (DAEC), n-alkyldimethylammonio propane carboxylate (DAPC), n-alkyl dimethylammonio methane sulfonate (DAMS), n-alkyl dimethylammonio ethane sulfonate (DAES), n-alkyl dimethylammonio propane sulfonate (DAPS), n-tetradecyl dimethylammonio propane sulfonate (TDAPS), n-tetradecyl dimethylammonio propane sulfonate (DDAPS), n-hexadecyl dimethylammonio propane sulfonate, n-alkyl dimethylammonio butane sulfonate (DABS), n-alkylamidomethane dimethylammonio methane carboxylate, n-alkylamido methane dimethylammonio ethane carboxylate, cocoamidopropylbetaine (CAPB), cocoamidosulfobetaine (CASB), laurylamidopropylbetaine (LAB), n-alkylamidomethane dimethylammonio methane sulfonate, n-alkylamidoethane dimethylammonio ethane sulfonate and n-alkylamidopropane dimethylammonio propane sulfonate.

27. The composition according to claim 22, wherein the at least one surfactant is a zwitterionic surfactant selected from the group consisting of N,N-dimethyl laurylamine N-oxide (DMLAO), N,N-dimethyl myristylamine N-oxide, N,N-dimethyl cetylamine N-oxide, N,N-dimethyl stearylamine N-oxide, 3-[(3-cholamidopropyl) dimethylammonio]-1-propanesulfonate (CHAPS) and 3-[(3-cholamidopropyl)-dimethylammonio]-2-hydroxy-1-propanesulfonate (CHAPSO).

28. The composition according to claim 22, wherein the at least one surfactant is selected from the group consisting of alkyltrimethylammonium hydroxides, cationic quaternary ammonium halides, and alkali metal salts of $C_{12}$–$C_{18}$ alkyl sulfates.

29. The composition according to claim 22, wherein the at least one surfactant is present at a concentration of about 10 to 40 grams per liter.

30. The composition according to claim 22, wherein the pH buffer is selected from the group consisting of 3-[cyclohexylamino]-1-propanesulfonic acid (CAPS), sodium borate, potassium carbonate, calcium carbonate and sodium carbonate.

31. The composition according to claim 22, wherein the pH buffer is present in the composition at a concentration of about 0.05 to 0.15M.

32. The composition according to claim 22, further comprising a base, said base being an alkali metal hydroxide or a tetraalkylammonium hydroxide having an alkyl group with from 1–4 carbon atoms.

33. The composition according to claim 32, wherein the base is present at a concentration of about 0.05 to 0.5 moles per liter and the cyanide salt is present at a concentration of about 0.5 to 5 grams per liter.

34. The composition according to claim 22, wherein the inorganic cyanide salt is selected from the group consisting of potassium cyanide, sodium cyanide, lithium cyanide and ammonium cyanide.

35. A method for determining hemoglobin in a whole blood sample comprising: a) mixing an aliquot of a whole blood sample with the reagent composition according to claim 1 or claim 22 to form a reaction mixture; and b) analyzing said reaction mixture on an automated hematology analyzer instrument to obtain a hemoglobin measurement.

36. The method according to claim 35, wherein a pH of the reagent composition is about 10.8 to less than about 11.2.

37. The method according to claim 35, wherein the at least one surfactant in the reagent composition is a zwitterionic surfactant selected from the group consisting of $C_8$–$C_{18}$ alkyl betaines, alkyl sulfobetaines, alkylamido betaines, alkylamido sulfobetaines, and combinations thereof.

38. The method according to claim 37, wherein the zwitterionic surfactant is selected from the group consisting of n-alkyldimethylammonio methane carboxylate (DAMC), n-alkyldimethylammonio ethane carboxylate (DAEC), n-alkyldimethylammonio propane carboxylate (DAPC), n-alkyl dimethylammonio methane sulfonate (DAMS), n-alkyl dimethylammonio ethane sulfonate (DAES), n-alkyl dimethylammonio propane sulfonate (DAPS), n-tetradecyl dimethylammonio propane sulfonate (TDAPS), n-tetradecyl dimethylammonio propane sulfonate (DDAPS), n-hexadecyl dimethylammonio propane sulfonate, n-alkyl dimethylammonio butane sulfonate (DABS), n-alkylamidomethane dimethylammonio methane carboxylate, n-alkylamido methane dimethylammonio ethane carboxylate, cocoamidopropylbetaine (CAPB), cocoamidosulfobetaine (CASB), laurylamidopropylbetaine (LAB), n-alkylamidomethane dimethylammonio methane sulfonate, n-allylamidoethane dimethylammonio ethane sulfonate and n-alkylamidopropane dimethylammonio propane sulfonate.

39. The method according to claim 35, wherein the at least one surfactant in the reagent composition is selected from the group consisting of N,N-dimethyl laurylamine N-oxide (DMLAO), N,N-dimethyl myristylamine N-oxide, N,N-dimethyl cetylamine N-oxide, N,N-dimethyl stearylamine N-oxide, 3-[(3-cholamidopropyl) dimethylammonio]-1-propanesulfonate (CHAPS) and 3-[(3-cholamidopropyl) dimethylammonio]-2-hydroxy-1-propanesulfonate (CHAPSO).

40. The method according to claim 35, wherein the at least one surfactant in the reagent composition is selected from the group consisting of alkyltrimethylammonium hydroxides, cationic quaternary ammonium halides, and alkali metal salts of $C_{12}$–$C_{18}$ alkyl sulfates.

41. The method according to claim 35, wherein the at least one surfactant in the reagent composition is present at a concentration of about 10 to 40 grams per liter.

42. The method according to claim 35, wherein the pH buffer in the reagent composition is selected from the group consisting of 3-[cyclohexylamino]-1-propanesulfonic acid (CAPS), sodium borate, potassium carbonate, calcium carbonate and sodium carbonate.

43. The method according to claim 35, wherein the pH buffer is present in the reagent composition at a concentration of about 0.05 to 0.15M.

44. The method according to claim 35, further comprising a base in the reagent composition, said base being an alkali metal hydroxide or a tetraalkylammonium hydroxide having an alkyl group with from 1–4 carbon atoms.

45. The method according to claim 35, wherein the inorganic cyanide salt in the reagent composition is selected from the group consisting of potassium cyanide, sodium cyanide, lithium cyanide and ammonium cyanide.

* * * * *